United States Patent [19]

Schwender et al.

[11] 4,018,825

[45] Apr. 19, 1977

[54] 5-HYDROXY-α-(SUBSTITUTED AMINOMETHYL)-M-XYLENE-α,α'-DIOLS

[75] Inventors: Charles F. Schwender, Lebanon; John Shavel, Jr., Mendham, both of N.J.

[73] Assignee: Warner-Lambert Company, Morris Plains, N.J.

[22] Filed: Apr. 7, 1976

[21] Appl. No.: 674,452

Related U.S. Application Data

[62] Division of Ser. No. 275,611, July 27, 1972.

[52] U.S. Cl. .................. 260/570.6; 260/471 R; 260/501.17; 260/501.18; 260/519; 424/309; 424/316; 424/330

[51] Int. Cl.[2] ........................................ C07C 91/22

[58] Field of Search ............... 260/501.17, 501.18, 260/570.6; 424/304, 316, 330

[56] References Cited

UNITED STATES PATENTS

| | | | |
|---|---|---|---|
| 3,631,108 | 12/1971 | Brandstrom et al. | 260/501.17 |
| 3,644,353 | 2/1972 | Luntz et al. | 260/570.6 X |

OTHER PUBLICATIONS

Bergman et al., "Experientia," vol. 25, pp. 899–901, (1969).
Bronchodilators, "Manufacturing Chemist and Aerosol News," vol. 40, p. 43, (1969).
Hartley et al., "Nature," vol. 219, pp. 861–863, (1968).

*Primary Examiner*—Robert V. Hines
*Attorney, Agent, or Firm*—Albert H. Graddis; Frank S. Chow; George M. Yahwak

[57] ABSTRACT

Compounds of the formula:

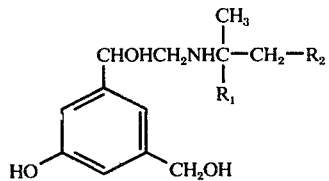

are disclosed, wherein $R_1$ and $R_2$ are hydrogen; or where $R_1$ is methyl, $R_2$ is hydrogen, phenyl, or phenyl substituted in the para-position by hydroxy, alkoxy, chloro, phenyl or alkyl having 1–6 carbon atoms. The compounds of this invention are useful in the treatment of bronchial asthma. These compounds exhibit unique biological properties in that they provide the desired bronchial dilation effect without accompanying cardiac stimulation.

1 Claim, No Drawings

5-HYDROXY-α-(SUBSTITUTED AMINOMETHYL)-M-XYLENE-α,α'-DIOLS

This is a division of application Ser. No. 275,611 filed July 27, 1972.

The present invention relates to novel compounds. More particularly, the present invention relates to compounds having the following structural formula:

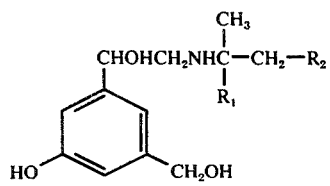

wherein $R_1$ and $R_2$ are hydrogen; or where $R_1$ is methyl, $R_2$ is hydrogen or phenyl substituted in the para-position by hydroxy, alkoxy, chloro, phenyl, or alkyl having 1–6 carbon atoms branched or straight chain.

Among the preferred species are those compounds wherein $R_1$ and $R_2$ are hydrogen; $R_2$ is hydrogen and $R_1$ is methyl; and where $R_1$ is methyl and $R_2$ is phenyl.

In addition, esters of the above compounds such as acetate, propionate, benzoate, succinate, as well as oxazolidine derivatives, are also features of this invention.

The compounds of this invention also form salts with pharmaceutically acceptable acids or bases and these salts are also included within the scope of this invention.

According to the present invention, the above compounds are prepared by reactions which are illustrated by the following reaction scheme:

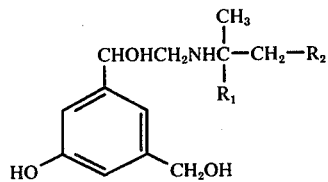

involve the formation of the mono methyl ester of 5-benzyloxyisophthalate (II). The intermediate 5-benzyloxy-3-carboxy-α-(methylsulfinyl)-acetophenone (III) is obtained by treatment of II with dimethylsulfinyl anion. Aqueous acetic acid treatment of III causes a Pummerer rearrangement of III and to give the methyl thiomethyl acetal (IV) and subsequent hydrolysis to the corresponding substituted phenylglyoxal product V. Reductive amination of IV or V with the appropriate amine and $KBH_4$ gives 3-benzyloxy-5-[2-(substituted amino)1-(hydroxy)ethyl]-benzoic acid, VI. Esterification of VI with methanol and ethanesulfonic acid gives the ester VII, which is reduced with $LiAlH_4$ to give VIII. Catalytic reduction debenzylates VIII and gives the desired product, IX.

The compound IX is also synthesized from dimethyl 5-hydroxy-isophthalate (X) by reaction with dimethylsulfinyl anion giving the intermediate methyl 5-hydroxy-3[α-(methylsulfinyl) acetyl]benzoate (XI). An acid-catalyzed Pummerer rearrangement of XI gives the corresponding methylthiomethyl acetal (XII) and subsequent hydrolysis to the corresponding substituted phenylglyoxal product, XIII. Reductive amination of XII or XIII with $LiAlH_4$ yields 5-hydroxy-α-(substituted aminoethyl)m-xylene α-α'-diol (IX).

Alternative, reductive amination of XII or XIII with

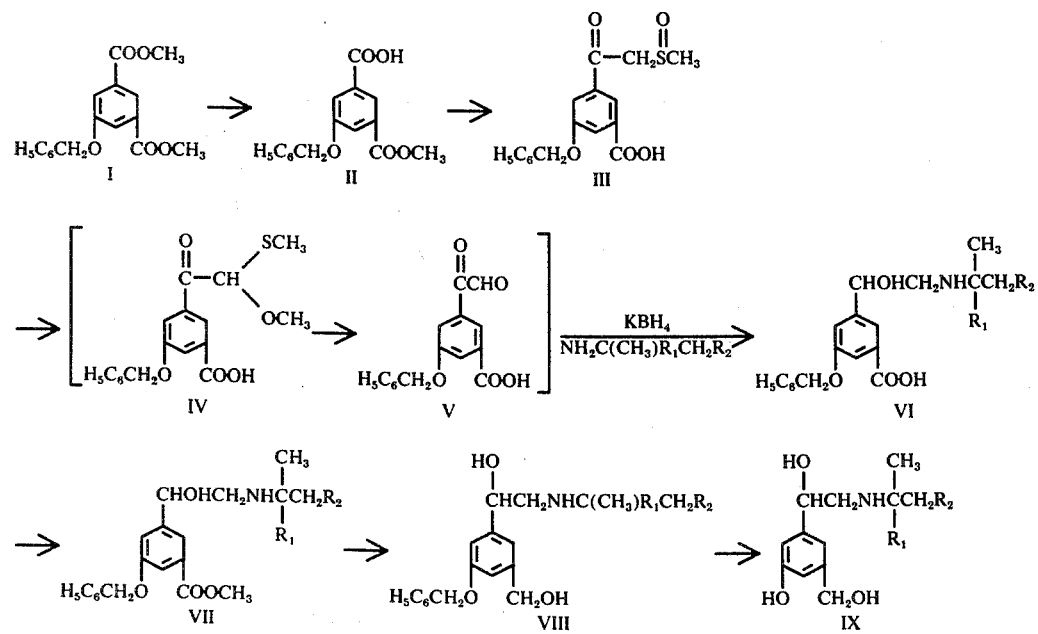

Referring now to the above reaction scheme, the synthesis of the compounds of the invention:

$KBH_4$ and the appropriate amine gives ester intermediate XIV. Reduction of XIV with $LiAlH_4$ gives IX.

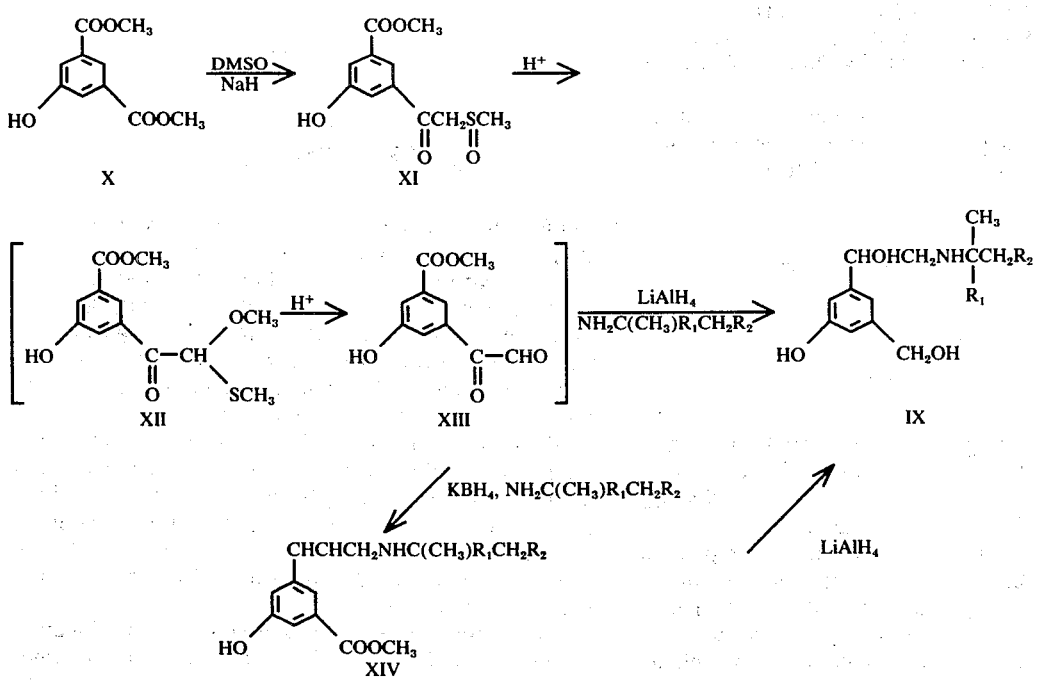

The compounds of this invention have bronchodilator (β-sympathomimetic) activity useful in the treatment of bronchial asthma and related bronchial spasms. In animals such as dogs, a dose of about 0.1–5 mg/kg (i.p.) is effective to prevent an increase in pulmonary resistance due to bronchial spasms induced by the aerosol administration of 1 mg of histamine. Minimal cardiac stimulant or heart rate increases are observed at this dosage level. The compounds exhibit the same potency in the guinea pig against aerosolized histamine. Further, these compounds selectively exert their therapeutic effect in the lung following either oral or parenteral administration.

The compounds of this invention are indicated in the treatment or management of bronchial asthma. The dose required is within the above-described dosage range which, of course, can be varied depending upon the severity of the condition being treated and the age and sex of the patient, by methods well known to the clinical arts.

In order to use these compounds they are combined with diluents such as lactose, dicalcium phosphate and compounded into dosage forms such as tablets by methods well known to the pharmacist's art. They can also be formulated as an aerosol by suspending the selected compound in a vehicle such as normal saline and formulated by standard pharmaceutical procedures.

In order to enhance and broaden the therapeutic spectrum of these compounds other therapeutic agents such as steroids, typically those derived from the cortisone series, may also be included in these dosage forms.

In order to further illustrate the practice of this invention, the following examples are included:

EXAMPLE 1

Dimethyl 5-benzyloxyisophthalate.

A mixture of 156 g (0.743 mole) of dimethyl 5-hydroxyisophthalate, 171 g (1 mole) of benzylbromide and 138 g (1 mole) of $K_2CO_3$ in 1 l. of acetone was refluxed for 18 hours. The reaction mixture was evaporated to a residue which was extracted with hot cyclohexane to give the crystalline product in a quantitive yield upon cooling. The analytical sample was obtained by recrystallization from cyclohexane, mp. 94–95°.

Anal. Calcd. for $C_{17}H_{16}O_5$: C, 67.99; H, 5.37; Found C, 68.09; H, 5.46.

EXAMPLE 2

Methyl 5-benzyloxyhydrogenisophthalate.

A mixture of 91.0 g (0.304 mole) of dimethyl 5-benzyoxisophthalate and 13.4 g (0.334 moles) of NaOH in 500 ml of MeOH was refluxed for 2.5 hrs. The mixture was evaporated to a residual solid which was dissolved in EtOAc (1 l.) and washed with $H_2O$ (2×500 ml). The aqueous phase was acidified with HCl and re-extracted with EtOAc (3×500 ml). After drying the EtOAc extract of acid phase with $MgSO_4$, evaporation of the EtOAc gave a crude white solid which was recrystallized from MeOH-$H_2O$ to give 70.1 g (80.5%) mp. 147°–150°. The analytical sample was obtained by recrystallization from MeOH-$H_2O$, mp. 154°–155°.

Anal. Calcd. for $C_{16}H_{14}O_5$: C, 67.13, H, 4.93. Found: C, 67.02; H, 4.99.

EXAMPLE 3

3-Benzyloxy-5-carboxy-α-(methylsulfinyl)-acetophenone.

To a mixture of DMSO (210 ml) and benzene (420 ml) heated with NaH, 57% in oil (13.0 g, 0.31 mole) for 1 hr. at 75° a DMSO solution (270 ml) containing 27.0 g (94.7 mmoles) of methyl 5-benzyloxyhydrogenisophthalate was added. The mixture was stirred at room temperature for 2 hrs. and then added to 3 l. of $Et_2O$. The Na salt was collected and dissolved in $H_2O$ (200 ml) which was then acidified to pH5 with HOAc. Cooling gave a yellow precipitate; yield 29.9 g (95.2%) mp. 128°–134°. Recrystallizations from 2-PrOH/hexane gave the analytical material, mp. 137°–140°dec.

Anal. Calcd. for $C_{17}H_{16}O_5S$: C, 61.43; H, 4.85; S, 9.65. Found: C, 61.13; H, 4.86; S, 9.57.

EXAMPLE 4

3-Benzyloxy-5-carboxyphenylglyoxal and 3-benzyloxy-5-carboxyphenylglyoxal methylthio-methyl acetal.

A mixture of 40.0 g (120 mmoles) of 3-benzyloxy-5-carboxy-α-(methylsulfinyl)acetophenone, 1.6 l. of 50% aqueous HOAC and 0.8 l. McOH was refluxed for 68 hrs. The mixture was extracted with $CHCl_3$ (1×3 l.). The $CHCl_3$ phase was dried with $MgSO_4$ and evaporated to give a quantitive yield of a light yellow solid, mp. 165°–168° which was purified by recrystallization from benzene-hexane, mp. 167°–169° dec.

EXAMPLE 5

3-Benzyloxy-5-[2-(isopropylamino)-1-hydroxyethyl]-benzoic acid.

The 3-benzyloxy-5-carboxyphenylglyoxal (;b 120 moles) was dissolved in MeOH (1 l.) and cooled to 0°. Isopropylamine (200 ml) was added at 0° and the resulting mixture was stirred at 0° for 1 hr. before $KBH_4$ (12.2 g, 228 moles) was added over a period of 2 hrs., portionwise. The resultant mixture was allowed to stir at room temperature overnight before it was evaporated to a residual glass. The residue was acidified with 6N HCl (1 l.) and extracted with $CHCl_3$( 1 142 l.). The solid HCl precipitated from the $CHCl_3$ extract upon standing; yield 21.9 g which gave 20.0 g (50%) mp. 290°–292° dec. of the free base upon stirring in aqueous $NH_4OH$ and collecting by filtration.

Anal. Calcd. for $C_{19}H_{23}NO_4$: C, 69.28; H, 7.04; N, 4.05. Found C, 68.74; H, 7.07, N, 4.01.

EXAMPLE 6

Methyl 3-benzyloxy-5-[2-(isopropylamino)-1-hydroxyethyl]-benzoate.

A mixture of 19.0 g (57.8 mmoles) of 3-benzyloxy-5-[2(isopropylamino)-1-hydroxyethyl]-benzoic acid and 7.7 g (70.0 mmoles) of ethanesulfonic acid was refluxed for 20 hrs. The mixture was then evaporated in vacuo and the residue obtained was dissolved in $CHCl_3$ (500 ml). After washing the $CHCl_3$ solution with 5% $NaHCO_3$( 1×250 ml) and drying with $MgSO_4$, the crude ester was obtained by evaporation of the $CHCl_3$, yield 17.5 g (88.3%). The analytical sample was obtained as the HCl salt from 2-PrOH/$Et_2O$, mp. 164°–165°.

Anal. Calcd. for $C_{20}H_{25}NO_4 \cdot HCl$: C, 63.24; H, 6.90; N, 3.69; Cl, 9.33. Found: C, 63.07; H, 6.99; N, 3.89; Cl, 9.15.

EXAMPLE 7

5-Benzyloxy-α-[(isopropylamino)methyl]-m-xylene-α, α'-diol.

To a suspension of $LiAlH_4$ (4.57 g, 120 moles) in anhydrous $Et_2O$ (0.5 l.) was added an ethereal solution (0.5 l.) of the methyl 3-benzyloxy-5-[2(isopropylamino)-1-hydroxyethyl]-benzoate (17.5 g, 50.9 mmoles) slowly at room temperature. The resultant mixture was heated at reflux for 4 hrs. The $LiAlH_4$ and complex was hydrolyzed by the slow addition of 40 ml of $H_2O$. The granular precipitate which formed was removed by filtration and an oily product was obtained from the ether filtrate after evaporation; yield 15.2 g.

(94.3%). The crude product was crystallized from $Et_2O$-hexane; yield 9.24 g (54.4%) mp. 84°–89°. The analytical sample was obtained from EtOAc-hexane, mp. 90°–93°.

Anal. Calcd. for $C_{19}H_{25}NO_3$: C, 72.35; H, 7.99; N, 4.44. Found C, 72.21; H, 8.17; N, 4.18.

EXAMPLE 8

5-Hydroxy-α-[(isopropylamino)methyl]-m-xylene-α, α'-diol hemifumarate.

An ethanol solution (200 ml) containing 9.34 g. (29.6 mmoles) of crystalline 5-benzyloxy-α-[(isopropylamino)methyl]-m-xylene-α, α'-diol was hydrogenated over 4.0 g of 10% Pd-C catalyst until hydrogen uptake had ceased (1 hr.). The catalyst was removed by filtration through a celite pad and the filtrate was evaporated to give an oily residual product. A crystalline fumarate salt was obtained; yield 6.71 g (82.0%) mp. 230°–245° dec. The analytical sample was obtained from MeOH-$Et_2O$; yield 6.13 g (73.2%) mp. 246°–248° dec.

Anal. Calcd. for $C_{12}H_{19}NO_3 \cdot 1/2C_4H_4O_4$: C, 59.25; H, 7.47; N, 4.94. Found: C, 59.28; H, 7.45; N, 4.80.

EXAMPLE 9

3-Benzyloxy-5-[2-(tert-butylamino-1-hydroxyethyl]-benzoic acid.

A solution of 3-benzyloxy-5-carboxyphenylglyoxal (120 mmoles) in MeOH (1 l.) was stirred at 0° for 1 hr. $KBH_4$ (12.2 g, 228 mmoles) was added at 0° in aliquots over a period of 3 hrs. and the resulting mixture was stirred at room temperature overnight. The mixture was evaporated in vacuo and the residue obtained was acidified with 3N HCl (400 ml). The aqueous mixture was extracted with $CHCl_3$ (3×500 ml). The $CHCl_3$ extracts were combined and ether was added after cooling. A white precipitate was collected; yield 23.6 g (51.8%) mp. 222°–225° dec of the product HCl salt. The analytical sample was obtained from 2PrOH/$E_2O$, mp. 228°–230° dec. The free base was obtained by stirring the salt in $NH_4OH$. Filtration gave 15.2 g (36.9%) mp. 270°–272° dec.

Anal. Calcd. for $C_{20}H_{25}No_4 \cdot HCl$: C, 63.24; H, 6.90; N, 3.69; Cl, 9.33. Found: C, 63.02; H, 7.04; N, 3.45; Cl, 9.36.

EXAMPLE 10

Methyl 3-benzyloxy-5-[2-(t-butylamino)-1-hydroxyethyl]-benzoate.

A mixture of 15.2 g (44.3 mmoles) of 3-benzyloxy-5-[2-(t-butylamino)-1-hydroxyethyl]-benzoic acid and 5.5 g (50 mmoles) of ethanesulfonic acid was heated at reflux for 20 hrs. in 300 ml of MeOH. The reaction mixture was evaporated in vacuo to give a crude oily residue which was partitioned between $CHCl_3$ (50 ml) and 5% $NaHCO_3$ 200 ml). The $CHCl_3$ phase was dried with $MgSO_4$ and evaporated to give a solid residue in a quantitative yield. A crystalline HCl salt was obtained from 2-PrOH/$Et_2O$, mp. 192°–195°.

EXAMPLE 10

5-Benzyloxy-α-[(t-butylamino)methyl]-m-xylene-α, α'-diol fumarate.

To a suspension of $LiAlH_4$ (3.42 g, 90 mmoles) in 300 ml of dry THF was added a THF solution (500 ml)

of the methyl 3-benzyloxy-5-[2(t-butylamino)-1-hydroxyethyl]benzoate (14.8 g, 41.3 mmoles). The reaction mixture was refluxed for 4 hrs. The LiAlH$_4$ and complex was hydrolyzed by the addition of 40 ml of H$_2$O, slowly. The granular precipitate which formed was removed by filtration and THF filtrate was evaporated to give 13.1 g (95.3%) of crude product as an oil. A crystalline fumarate salt was obtained from MeOH-Et$_2$O; yield 10.7 g (66.8%) mp. 195°–200° dec.

Anal. Calcd. for $C_{20}H_{27}NO_3 \cdot 1/2\, C_4H_4O_4$: C, 68.20; H, 7.54; N, 3.61. Found: C, 67.79; H, 7.68; N, 3.40.

EXAMPLE 12

α-[(t-butylamino)methyl]-5-hydroxy-m-xylene-α, α'-diol hemifumarate.

An ethanolic solution (200 ml) containing 5-benzyloxy-α-[(t-butylamino) methyl]-m-xylene-α, α'-diol (8.25 g, 25.1 mmoles) was hydrogenated over 4.0 g of 10% Pd-C catalyst until hydrogen uptake had ceased (1 hr.). The catalyst was removed by filtration through a celite pad and the EtOH filtrate was evaporated to give an oily residual product; yield 5.75 g (95.9%). A crystalline hemifumarate salt was obtained from MeOH-Et$_2$O; yield 5.06 g (67.9%) mp. 249°–251° dec. The analytical sample was obtained by recrystallization from MeOH-Et$_2$O; yield 3.33 g (44.7%) mp. 263°–265° dec.

Anal. Calcd. for $C_{13}H_{21}NO_2 \cdot 1/2\, C_4H_4O_4$: C, 60.59; H, 7.80; N, 4.71. Found: C, 60.79; H, 7.88; N, 456.

EXAMPLE 13

Methyl 3-benzyloxy-5-[(2-(1,1 dimethyl-2-phenylethylamino)1-hydroxyethyl]-benzoate.

The 3-benzyloxy-5-carboxyphenylglyoxal (120 mmoles) was dissolved in MeOH (1 l.) and cooled to 0°. 1,1,-Dimethyl-2-phenyl-ethylamine (100 g, 0.67 moles) was added at 0° and the resulting mixture was stirred at 0° for 1 hr. before addition of KBH$_4$ (12.2 g, 228 mmoles) over a period of 2 hrs. portionwise. The resultant mixture was allowed to react at room temperature for 18 hours before it was evaporated to a residual glass. The residue was acidified with 6N HCl (1 l.) and extracted with CHCl$_3$ (1 l.). Addition of ether to the CHCl$_3$ extract gave the 1,1-dimethyl-2-phenylethylamine HCl as a white precipitate which was removed by filtration. The CHCl$_3$ filtrate was evaporated to give the crude 3-benzyloxy-5-[2-(1,1dimethyl-2-phenylethylamino)-1 -hydroxyethyl]benzoic acid HCl. The base was obtained by treating the crude salt with conc. NH$_4$OH, extracting with CHCl$_3$ and drying with MgSO$_4$ before evaporation to give the crude oily base.

A mixture of 3-benzyloxy-5-[2-(1,1-dimethyl-2-phenylethyl)-2-hydroxyethyl]-benzoic acid (120 mmoles) and 17.7 g (160 mmoles) of enthanesulfonic acid was heated at reflux for 18 hours in 500 ml of MeOH. The reaction mixture was evaporated to a residual oil which was dissolved in CHCl$_3$ (200 ml) and washed with 5% NaHCO$_3$ (2×200 ml). The CHCl$_3$ phase was dried (MgSO$_4$) and evaporated to give the crude, oily methyl 3-benzyloxy-5-[(1,1-dimethyl-2-phenylethylamino)-2-hydroxyethyl]-benzoate which was converted to a crystalline hemifumarate salt; yield 14.7 g (28.8%) mp. 173°–175° dec.

Anal. Calcd. for $C_{27}H_{31}NO_4 \cdot 1/2\, C_4H_4O_4$: C, 70.86; H, 6.77;, N, 2.85. Found: C, 70.90; H, 6.89; N, 2.73.

EXAMPLE 14

5-Benzyloxy-α-[(1,1-dimethyl-2-phenylethylamino)-metyl]-m-xylene-α, α'-diol.

To a suspension of 1.97 g (52.0 mmoles) of Lithium Aluminum Hydride in 500 ml of Et$_2$O, was added an ether solution of the free base ester 11.1 g (25.6 mmoles) and the resulting suspension was refluxed for 4 hours before 2H$_2$O (5 ml) was added to destroy the LiAlH$_4$ and complex. The white precipitate was filtered and the Et$_2$O filtrate was evaporated to give the crude product as an oil in a quantitive yield. The product was purified as a crystalline hemifumarate salt; yield 11.2 g (94.4%) mp. 190°–193° dec. The analytical material had a mp. of 193°–194°.

Anal. Calcd. for $C_{26}H_{31}NO_3 \cdot 1/2 C_4H_4O_4$: C, 72.55; H, 7.18; N, 3.02. Found: C, 72.39; H, 7.30; N, 2.84.

EXAMPLE 15

α-[(1,1-Dimethyl-2-phenylethylamino)methyl]-5-hydroxy-m-xylene-α, α'-diol hemifumarate.

An ethanolic solution (200 ml) of the benzyloxy intermediate 8.73 g (21.4 mmoles) was hydrogenated over 4.0 g of 10% Pd-C catalyst until hydrogen uptake had ceased (1 hr). The mixture was filtered through celite and the filtrate was evaporated and gave an quantitative yield of the free base product as a clear oil. A white crystalline hemifumarate salt was obtained; yield 6.62 g (82.3%) mp. 209°–212° dec. The analytical sample was obtained by recrystallization from MeOH-Et$_2$0; yield 5.69 g (70.8%) mp. 214°–215.5° dec.

Anal. Calcd. for $C_{29}H_{25}NO_3 \cdot 1/2 C_4H_4O_4$: C, 67.54; H, 7.29; N, 3.75. Found: C, 67.45; H, 7.53; N, 3.67.

EXAMPLE 16

Methyl 3-[α-(methylsulfinyl)acetyl]-5-hydroxy-benzoate.

To a cold suspension of NaH (105 mmole) in 71 ml of DMSO and 71 ml of benzene was added slowy 10.0 g (47.6 mmoles) of dimethyl 5-hdyroxylisophthalate dissolved in 25 ml of DMSO and 25 ml of benzene. The resulting mixture was then heated at reflux for 1.5 hrs. cooled and acidified with 100 ml of 40% HOAc. The aqueous phase was separated and extracted with the CHCl$_3$ (3×250 ml). The combined organics were dried (MgSO$_4$) and distilled off under vacuum giving a gummy residue. The crude gum was washed with hexane (2×20 ml) and triturated with EtOAc (10 ml) with heat. Cooling gave 4.20 g (35%) of a yellow solid, mp. 144°–150°. Recrystallizations from EtOAc-hexane gave the analytical sample, mp. 153°–155°.

Anal. Calcd. for $C_{11}H_{12}O_5S$: C, 51.55; H, 4.72;, S, 12.51. Found: C, 51.84; H, 4.90; S, 12.64.

EXAMPLE 17

Methyl 3-[2-(t-butylamino)-hydroxyethyl]-5-hydroxybenzoate.

A reaction mixture containing 4.20 g (16.4 mmoles) of methyl 3-[α-(methylsulfinyl)acetyl]-5-hydroxybenzoate, 100 ml of MeOH and 100 ml of 1N HCl was heated at reflux for 2 hrs. The mixture was extracted with CHCl$_3$ (3×200 ml) and the CHCl$_3$ extract was dried with MgSO$_4$. Evaporation of the volatile components gave the crude 3-carboxymethyl-5-hydroxyphenylglyoxal in a quantitative yield.

A methanolic solution (100 ml) containing the crude substituted phenylglyoxal was cooled to 0° and 20 ml of t-butylamine was added. After stirring the mixture at 0° for 1 hr., KBH$_4$ (1.78 g, 33 mmoles) was added in 4 aliquots over a 2 hr. period. The mixture was allowed to reach room temperature and stir overnight.

The reaction mixture was evaporated in vacuo and the residue obtained was suspended in 6N HCl (100 ml) and washed with CHCl$_3$ (2×50 ml). The acidic phase was basified with NH$_4$OH and extracted with EtOAc (3×200 ml). The EtOAc extracts were dried (MgSO$_4$) and evaporated to give the crude product as an oil; yield 1.35 g (31%). The product was purified as a hemifumarate salt from MeOH/Et$_2$O, mp. 261°–262.5° dec.

Anal. Calcd. C$_{14}$H$_{21}$NO$_4$.1/2C$_4$H$_4$O$_4$: C, 59.07; H, 7.13; N, 4.31. Found: C, 59.16; H, 7.19; N, 4.17.

EXAMPLE 18

To illustrate the in vivo effects, compounds wherein R$_1$ is methyl and R$_2$ is hydrogen; R$_1$ is methyl and R$_2$ is phenyl; and R$_1$ and R$_2$ are hydrogen are tested in dogs which are challenged by the aerosol administration of 1 mg of histamine. These compounds are identified as W9803A, W9890A, and 9640A respectively in the following table:

TABLE

| | | *in vivo* (Dog) 1 mg Histamine (Aerosol) | | |
|---|---|---|---|---|
| | | Δ HR./Min. | % Protection From Histamine | |
| Compound | Dose (ip) | (Over Controls) | 15 Min. | 1 Hr. |
| salbutamol | 3.12 μg/kg | 17 | 85% | 48% |
| Th1165a | 3.12 μg/kg | 45 | 85% | 84% |
| W9640A | 5 mg/kg | 28 | 91% | 90% |
| W9803A | 0.3 mg/kg | 5 | 91% | 69% |
| W9890A | 1.25 mg/kg | 4 | 91% | 88% |

NOTE:
Doses chosen for salbutamol and Th1165a still demonstrated a dose-response relationship and were not on the upper right flat portion of the dose-response curve for the dilation vs. dose.
Δ HR./Min. = Change in heart rate per minute.

While salbutamol and Th1165a are more potent bronchodilators than the compounds of this invention, these known compounds also exhibit the undesirable cardiac stimulatory effect. Consequently, the compounds of this invention possess unique therapeutic properties over these known bronchodilators in that they do not produce significant heart stimulatory actions.

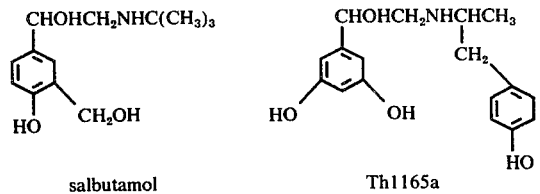

salbutamol          Th1165a

We claim:
1. 5-benzyloxy-α[(-butylamino)methyl]-m-xylene-α,α′-diol.

* * * * *